(12) United States Patent
Chang et al.

(10) Patent No.: US 8,821,942 B1
(45) Date of Patent: Sep. 2, 2014

(54) HIGHLY COMPRESSIBLE, LOW DENSITY GROUND CALCIUM CARBONATE GRANULATION AND A RELATED METHOD OF PREPARATION

(75) Inventors: David S. Chang, Fullerton, CA (US); Huoy-Jiun Jean Wang, Murrieta, CA (US)

(73) Assignee: Access Business Group International LLC, Ada, MI (US)

( * ) Notice: Subject to any disclaimer, the term of this patent is extended or adjusted under 35 U.S.C. 154(b) by 52 days.

(21) Appl. No.: 13/440,309

(22) Filed: Apr. 5, 2012

Related U.S. Application Data (60) Provisional application No. 61/472,355, filed on Apr. 6, 2011.

(51) Int. Cl.
*A61K 9/14* (2006.01)

(52) U.S. Cl.
USPC ............ 424/492; 424/687; 424/493; 424/495

(58) Field of Classification Search
None
See application file for complete search history.

(56) References Cited

U.S. PATENT DOCUMENTS

| | | |
|---|---|---|
| 7,883,552 B2 | 2/2011 | Lang et al. |
| 2007/0190020 A1 * | 8/2007 | Hrakovsky et al. ........ 424/78.27 |
| 2009/0252805 A1 * | 10/2009 | Piene ........................... 424/490 |

OTHER PUBLICATIONS

Gum Arabic, available at http://en.wikipedia.org/wiki/Gum_arabic, as retrieved Oct. 30, 2013.*

* cited by examiner

*Primary Examiner* — Robert T Crow
*Assistant Examiner* — Daniel F Coughlin
(74) *Attorney, Agent, or Firm* — Warner Norcross & Judd LLP (57) ABSTRACT

A calcium carbonate granulation and a method for preparing a calcium carbonate granulation are provided. The method includes applying an atomized binder to powdered calcium carbonate in a fluid bed granulator at a relatively high atomization pressure to achieve a reduced binder droplet size, and drying the resulting composition at elevated temperatures in a fluidized bed dryer. The resulting granulation include porous granules having a lower density and reduced mean particle size with improved compressibility. In addition, the resulting granulation can be compacted into tablets having a hardness 50% greater than the hardness of tablets formed from commercially available granulations.

20 Claims, 12 Drawing Sheets

Calcium Carbonate Fluid Bed
Granulation Parameters

| Lot# | Inlet Temp (F) | Spray Rate (g/min) | Atomization Pressure (bar) | Bulk Density (g/cc) |
|---|---|---|---|---|
| Omya-1 | 180 | 16.6 | 2.0 | 0.547 |
| Omya-2 | 180 | 30 | 2.0 | 0.678 |
| Omya-3 | 180 | 16.6 | 0.5 | 0.594 |
| Omya-4 | 180 | 30 | 0.5 | 0.82 |
| Huber-1 | 180 | 16.6 | 2.0 | 0.69 |
| Huber-2 | 180 | 16.6 | 0.5 | 0.757 |
| Huber-3 | 180 | 30 | 2.0 | 0.862 |

Omya-1 Calcium Carbonate Granulation

Fig. 3

Omya-2 Calcium Carbonate Granulation

Fig. 4

Omya-3 Calcium Carbonate Granulation

Fig. 5

Huber-1 Calcium Carbonate Granulation

Fig. 6

Huber-2 Calcium Carbonate Granulation

Fig. 7

Huber-3 Calcium Carbonate Granulation

Fig. 8

Supplier 1 Calcium Carbonate Granulation

Fig. 9

Supplier 2 Calcium Carbonate Granulation

Calcium Carbonate Pilot Fluid Bed Granulation Parameters

| Lot# | Inlet Temp(°C) | Spray Rate (g/min) | Atomization Pressure (psi) | Product Temp (°C) | Bulk Density (g/cc) |
|---|---|---|---|---|---|
| Vector C1 | 65-80 | 125 | 39.0 | 35-55 | 0.591 |
| Vector C2 | 70-85 | 250 | 39.0 | 30-50 | 0.912 |

HIGHLY COMPRESSIBLE, LOW DENSITY GROUND CALCIUM CARBONATE GRANULATION AND A RELATED METHOD OF PREPARATION

BACKGROUND OF THE INVENTION

The present invention relates to compressible, low density ground calcium carbonate and a related method of preparation.

Calcium carbonate is widely used in the manufacture of pharmaceutical, nutraceutical and vitamin tablets. For example, calcium carbonate is an active ingredient in non-prescription antacids and oral calcium supplements. In the manufacture of these tablets, calcium carbonate originates as a powder lacking cohesiveness and compactability. Accordingly, tablet manufacturing typically includes a granulation process to convert powdered calcium carbonate into granules that are compactable into tablets.

Granulation processes include both dry granulation and wet granulation. Dry granulation includes aggregating powdery particles under high pressure without the application of moisture or heat. Wet granulation is more commonly used over dry granulation, and includes the wetting of powdery particles with a binder before drying and sieving the resulting granules. Known wet granulation processes include high shear granulation, extrusion and spheronization, and spray drying. However, calcium carbonate granules that are formed according to these known processes generally exhibit high densities, ultimately inhibiting their compressibility into tablets of a satisfactory hardness. In addition, calcium carbonate granules formed according to these known processes can exhibit small pore size, low porosity, and unsatisfactory surface area.

Accordingly, there remains a need for an improved system and method for forming compressible calcium carbonate. In particular, there remains a need for an improved system and method for preparing a highly compactable calcium carbonate that can be implemented across a range of pharmaceutical, nutraceutical and supplement formulations.

SUMMARY OF THE INVENTION

A calcium carbonate granulation and a method for preparing a calcium carbonate granulation are provided. The method generally includes applying a unique combination of atomization pressures, spray rates, binders and/or drying temperatures to form a calcium carbonate granulation having improved compressibility and tablet hardness over tablets formed from commercially available granulations.

In one embodiment, the method includes fluidizing calcium carbonate with heated inlet air, applying an atomized binder at a relatively high atomization pressure, and drying the resulting composition at elevated temperatures. The binder solution can be applied in a fluidized bed granulation process with an atomization pressure of between about 1.8 bar and about 2.2 bar and a spray rate of between about 12 g/min and 20 g/min. Fluidized bed inlet air can be heated to between about 120° F. and about 240° F., and optionally between about 130° F. and about 200° F., to dry the particulate granules. The resulting granulation can achieve a bulk density of less than about 0.8 g/cm³, and can be compressed into a tablet exhibiting improved hardness over tablets formed from commercially available granulations.

In another embodiment, the binder solution can be applied in a fluidized bed granulation process with an atomization pressure of between about 1.5 bar and about 4.5 bar, and optionally between about 2.0 bar and about 3.5 bar, and a spray rate of between about 75 g/min and about 200 g/min, and optionally between about 125 g/min and about 175 g/min. Fluidized bed inlet air can be heated to between about 120° F. and about 240° F., and optionally between about 130° F. and about 200° F., to dry the particulate granules. The resulting granulation can achieve a bulk density of less than about 0.8 g/cm³, and can be compressed into a tablet exhibiting improved hardness over tablets formed from commercially available granulations.

In another embodiment, a calcium carbonate granulation is provided. The granulation can include about 90% to about 99% by weight of calcium carbonate and about 1% to about 10% by weight of one or more binders. For example, the granulation can include about 92% to about 96% by weight of calcium carbonate, about 2% to about 4% by weight of maltodextrin binder, and about 2% to about 4% by weight of acacia binder. The particulate granules include a mean particle size of about 200 mesh, and the granulation includes a bulk density of between about 0.5 g/cm³ and about 0.8 g/cm³. The granulation is compactable into 500 mg tablet form on a Kikisui Vela G tablet press at 40 rpm, having a hardness that increases generally linearly from about 17 Strong-Cobb unit (scu) for a compression force of 10 kN to about 53 scu for a compression force of 40 kN.

Embodiments herein can provide granules with lower density, smaller overall particle size, increased porosity, and higher surface area that exhibit superior compressibility. In particular, the embodiments can provide fluid bed granulation parameters that are modified to include new slower binder spray rates, high spray atomization pressures, high drying air flow rates and higher drying air temperatures to achieve smaller granule sizes and more porous granules. The resulting granulation is well suited for compaction into tablets having a hardness of about 50% to about 129% greater than the hardness of tablets formed from commercially available granulations.

These and other features and advantages of the present invention will become apparent from the following description of the invention, when viewed in accordance with the accompanying drawings and appended claims.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE CURRENT EMBODIMENT

The current embodiment as contemplated and disclosed herein includes a compressible, low density granulation and a method for preparing a compressible, low density granulation. The method generally includes, within a fluidized bed granulation process, applying an atomized binder at a relatively high atomization pressure and a reduced spray rate, while drying the fluidized composition at elevated temperatures. The resulting low density granulation is compressible into tablets exhibiting improved hardness over tablets formed from commercially available granulations.

In one embodiment, the method for preparing a compressible, low density granulation includes selecting a powdered calcium carbonate for processing. The powdered calcium carbonate can include a mean particle size of between about 0.1 microns to about 250 microns, inclusive. Further optionally, the powdered calcium carbonate can include a mean particle size of between about 5 microns to about 15 microns inclusive, or about 10 microns to about 13 microns inclusive. Other particle sizes within or outside of these ranges also can be implemented depending on the application. One exemplary suitable powdered calcium carbonate can include a mean particle size of 12 microns and a bulk density of 1.5 g/cm$^3$, available as HuberCal® 250 by J. M. Huber Corporation of Edison, N.J., and as OmyaCal® FG-15 calcium carbonate from Omya International AG of Otringen, Switzerland with a median particle diameter of 15 microns.

Once selected, the powdered calcium carbonate is converted into a compressible form through fluidized bed granulation. Fluidized bed granulation is generally performed using a fluidized bed dryer having a fluid bed chamber, a blower, an exhaust filter, and one or more spray nozzle outlets. The product container houses the powdered calcium carbonate and is generally below a diverging portion of the fluid bed chamber. The blower provides a source of positive pressure to fluidize the powdered calcium carbonate upwardly into the diverging fluid bed chamber, where the particles are wetted with a binder solution from the spray nozzle or nozzles. The wet granules are dried by the heated air from the blower. The binder solution, sometimes referred to as a granulation solution, facilitates the binding of individual particles into larger granules. Once the binder solution is exhausted, or once the fluidized granules achieve the desired particle size, the fluidized granules are dried to a desired moisture level with a heated gas, typically air, from the inlet blower. A suitable granulator can include, for example, a Strea-1 fluid bed granulator from GEA Process Engineering, Inc., of Columbia, Md. or an FL-M-15 fluid-bed granulator by Freund-Vector Corporation of Marion, Iowa.

The binder solution can include a variety of compositions, and can be applied at a variety of flow rates and pressures. For example, the binder solution can include one or more binders, for example maltodextrin, dextrin, ethylcellulose, methylcellulose, hypromellose, hydroxylpropyl cellulose, sodium carboxymethyl cellulose, polyvinylpyrrolidone and hydrocolloids such as acacia, alginates, carrageenan, dextran, furcellaran, pectin, gelatin, gum agar, locust bean gum, gum ghatti, guar gum, tragacanth, gum Arabic, xanthan gum, karaya gum, tara gum, cellulose derivatives, starch derivatives, combinations thereof, and optionally any additional binder constituents set forth in U.S. Pat. No. 7,883,552 to Lang et al, which is hereby incorporated by reference in its entirety.

The granulation generally can include between about 1% and 25% by weight of binder, optionally between 2% and 10% by weight of binder, and further optionally between about 4% and about 8% by weight of binder. In one embodiment, for example, the granulation includes 5.7% by weight of binder, optionally 2.85% by weight of maltodextrin and 2.85% by weight of acacia. Optionally, other materials may also be added to the granulation, including for example active agents, medicaments, drugs, minerals, vitamins, supplements, diluents, glidants, lubricants, disintegrants, colors, flavors, sweeteners, and solubility retarding agents.

As noted above, the binder solution can be applied at a variety of flow rates and pressures. In some embodiments, the binder solution is applied at a relatively low flow rate and at a relatively high atomization pressure to deliver smaller droplet sizes of binder solution. For example, in some small scale embodiments the binder solution can be applied at a flow rate (i.e., a spray rate) of between 6 g/min and 30 g/min, optionally between about 12 g/min and 20 g/min, and further optionally about 16 g/min. In other large scale embodiments the binder solution can be applied at a flow rate of between 75 g/min and 250 g/min, optionally between about 125 g/min and about 200 g/min, further optionally between about 100 g/min and 175 g/min, even further optionally between about 110 g/min and 150 g/min, still further optionally between optionally about 115 g/min and 135 g/min, and yet further optionally about 125 g/min. In some applications, a spray rate of greater than 250 g/min is undesirable, as it can result in the formation of overly dense granules in the pilot fluid bed chamber. In addition, the outlet or nozzle pressure can include an atomization pressure (i.e., a nozzle pressure) of between about 1.5 bar and about 4.5 bar, optionally between about 1.8 bar and about 3.5 bar, further optionally between about 2.5 bar and 2.75 bar, and further optionally about 2.7 bar. The outlet or nozzle can assume a range of positions to wet particulates as they circulate in the fluid bed chamber. In addition, the binder can be heated to a temperature of at least 110° F., optionally to between 115° F. and 250° F., further optionally to between 130° F. and 200° F., even further optionally between about 140° F. and 158° F., and still further optionally about 150° F. The discharge of binder solution generally continues until all of the solution has been sprayed into the batch. During this spraying process, the calcium carbonate will generally aggregate into larger and larger granules, while the fluidized granules are dried as inlet air is heated and introduced through the granulator until the desired granule moisture level is achieved, typically below 1%.

In the present embodiment, the blower inlet air temperature and the blower inlet air flow rate are relatively high to achieve lower densities, smaller granule size and more porous granules. For example, the inlet air temperature can be between about 120° F. and about 240° F., optionally between about 130° F. and about 200° F., further optionally between about 140° F. and about 180° F., and still further optionally between about 150° F. and 180° F. Other inlet temperatures within or outside of these ranges also can be implemented depending on the application.

Though described as pertaining to fluidized bed granulation, other wet granulation methods, including high sheer batch or continuous granulation processes, may also achieve the desired physical properties of the granulation. In the present embodiment, the resulting granulation can be well suited for compaction into tablets. Generally, the granulations include a lower density, a smaller overall particle size, and an increased porosity relative to existing calcium carbonate granulations. In addition, it is believed that the granulations have other favorable characteristics, including a faster disintegration and dissolution and an improved mouth feel and texture.

Figure 1:
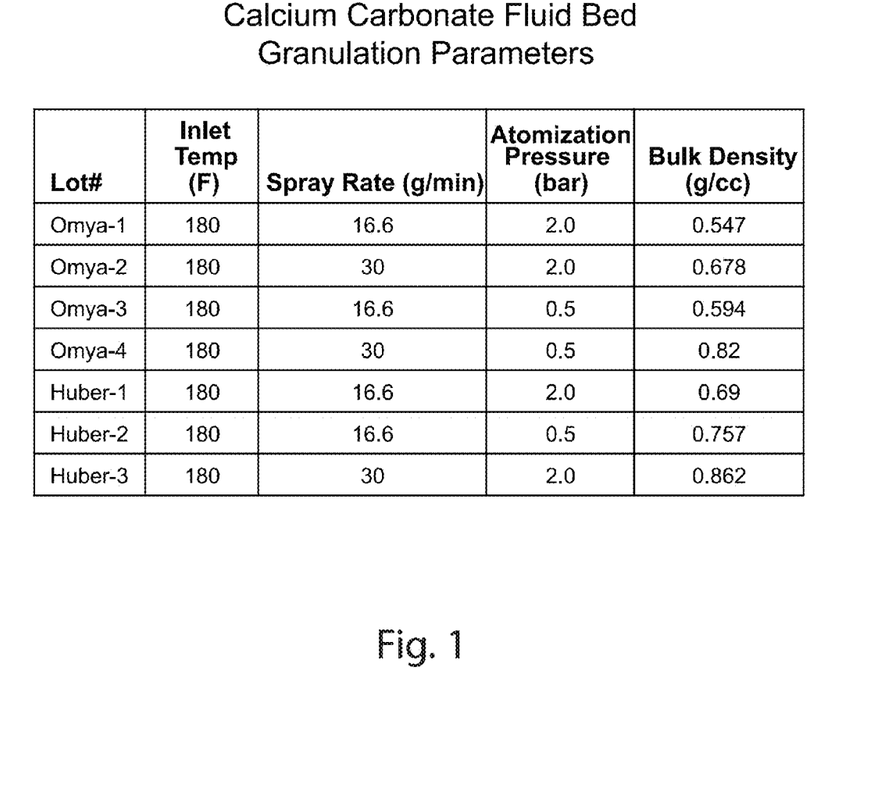
FIG. 1 is a table illustrating fluid bed granulation parameters in accordance with current embodiments.
Figure 2:
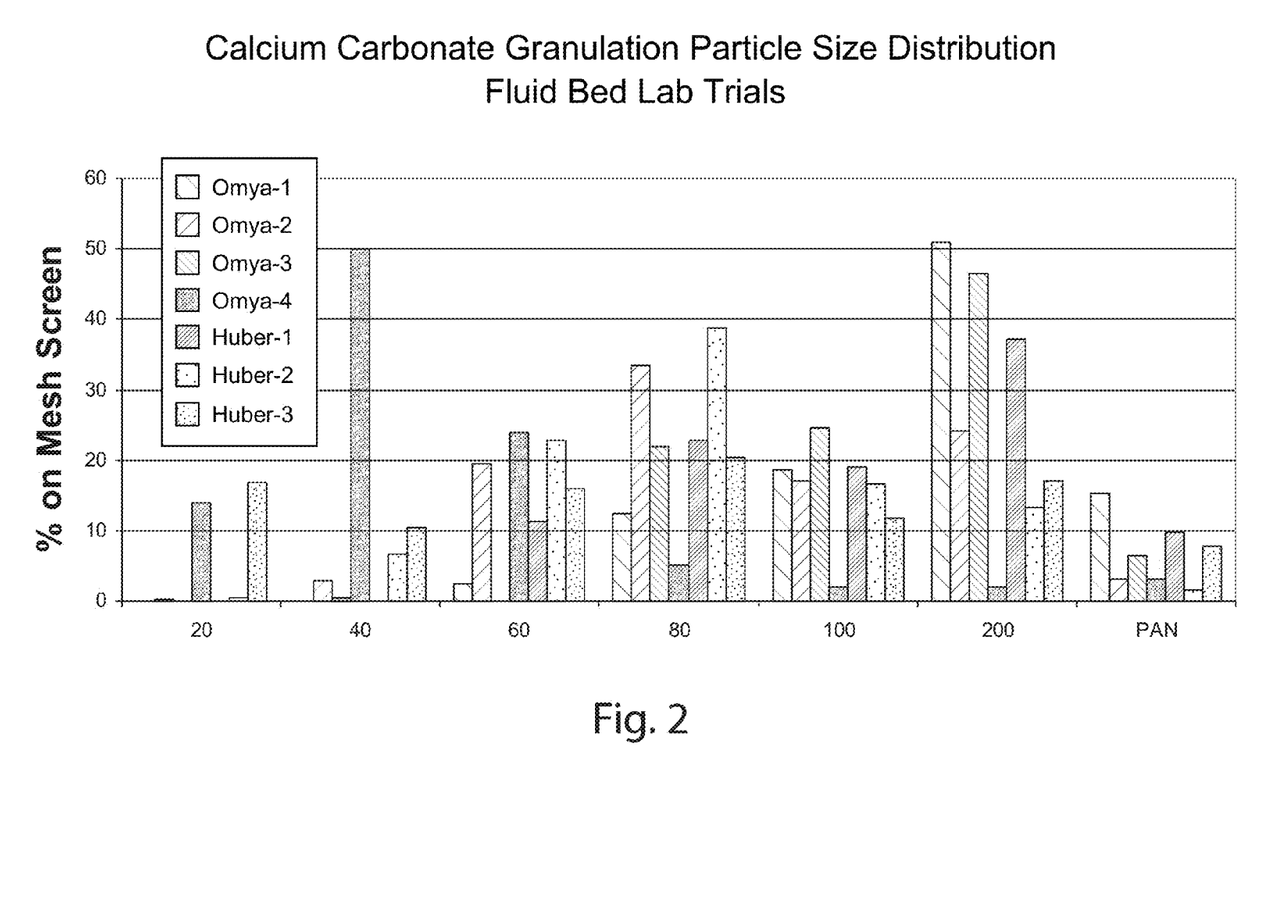
FIG. 2 is a bar graph illustrating particle size distributions for the granulations of FIG. 1.
Figure 3:
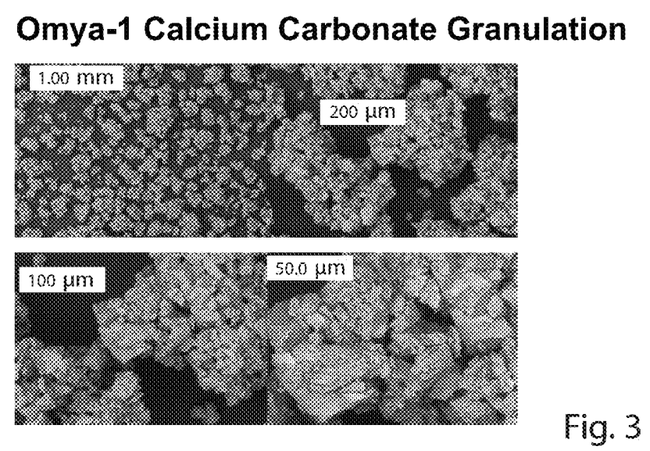
FIGS. 3-8 are SEM micrographs of granulations formed in accordance with the parameters of FIG. 1.
Figure 4:
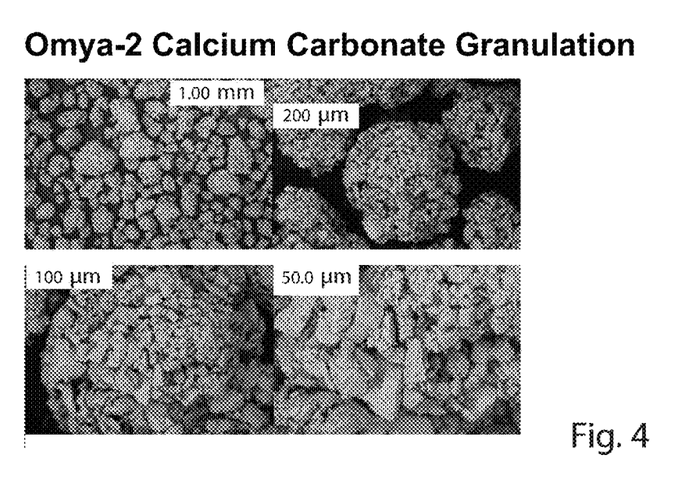
Figure 5:
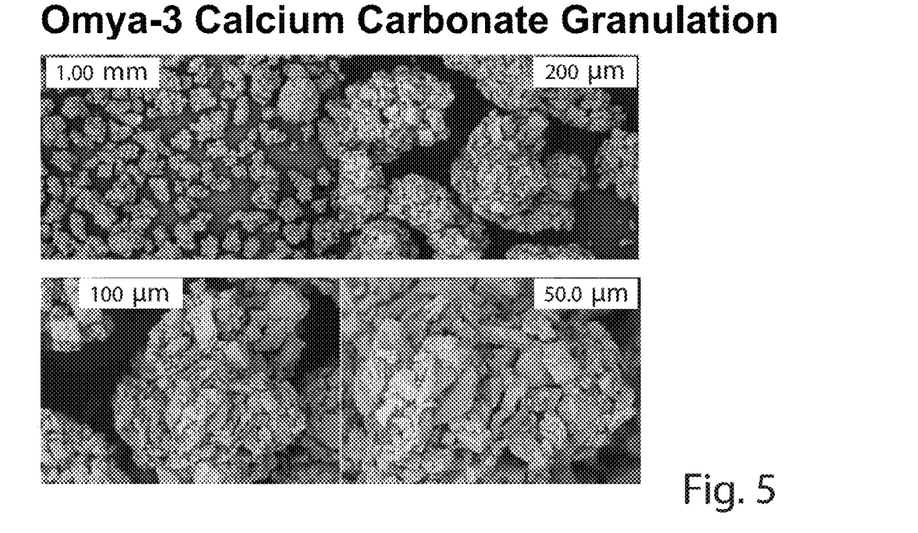
Figure 6:
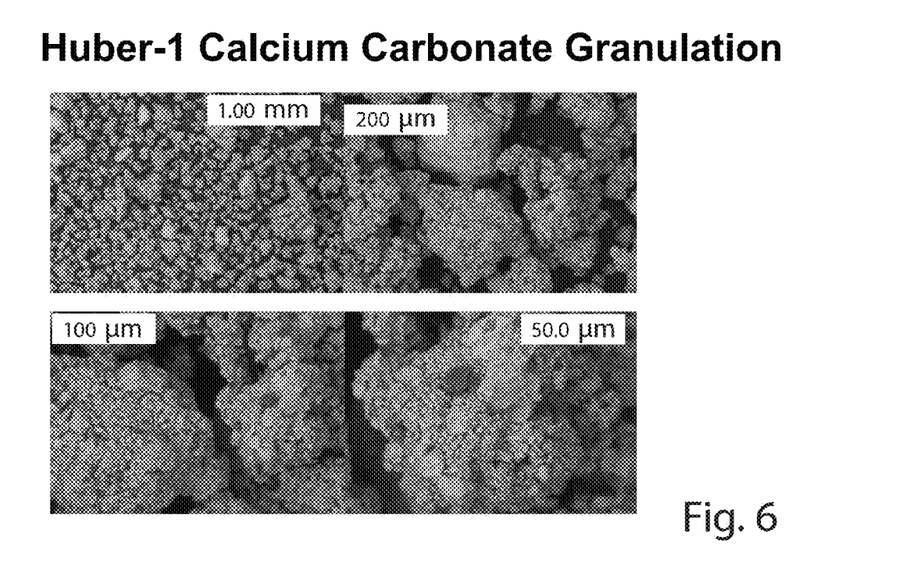
Figure 7:
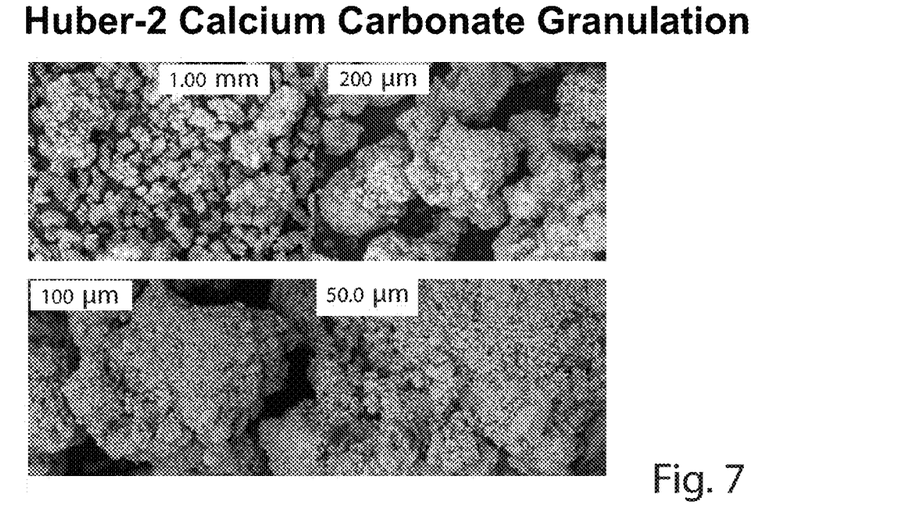
Figure 8:
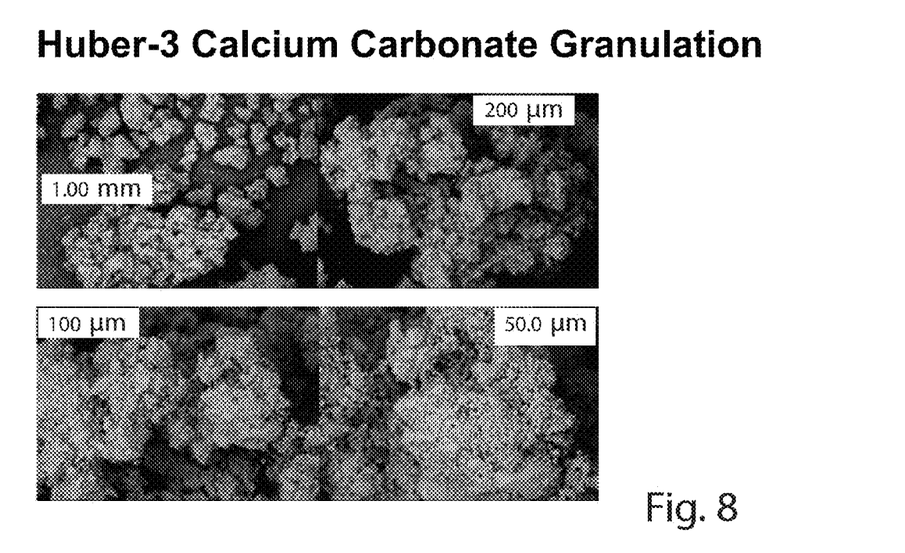
Figure 9:
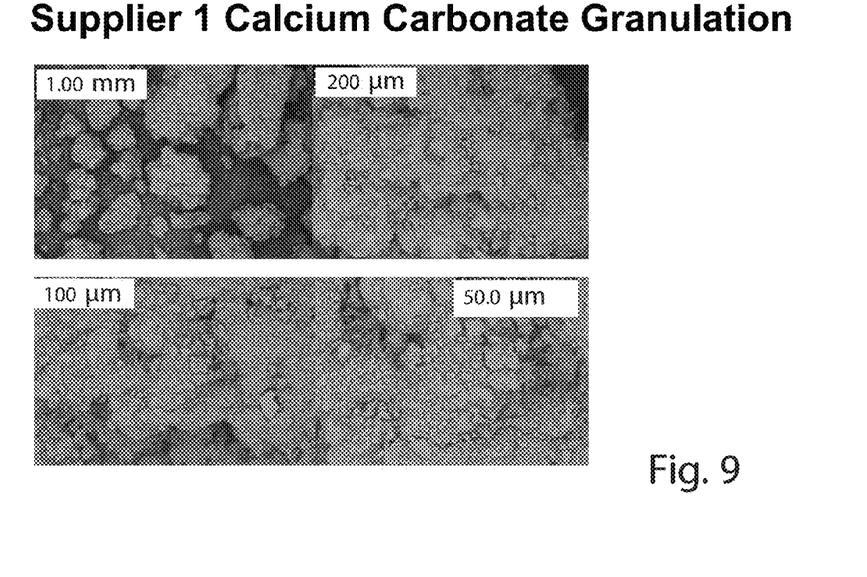
FIGS. 9-10 are SEM micrographs of calcium carbonate granulations from outside suppliers.
Figure 10:
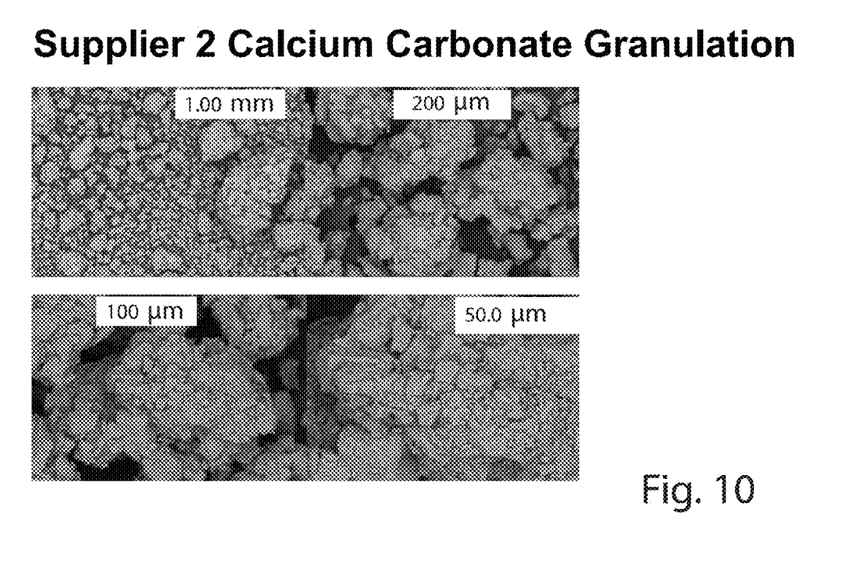

Calcium carbonate granulations formed in accordance with embodiments herein can include a bulk density less than about 0.8 g/cm$^3$, optionally less than about 0.7 g/cm$^3$ and further optionally less than about 0.6 g/cm$^3$. As shown in FIG. 1 for example, two calcium carbonate granulations achieved a bulk density of about 0.547 g/cm$^3$ and about 0.69 g/cm$^3$ respectively for a spray rate of about 16.6 g/min and an atomization pressure of about 2.0 bar. When granulation parameters were run at lower atomization pressures and/or higher spray rates as also shown in FIG. 1, the densities of the granules increased, the overall particle size increased, and the compressibility was reduced. As shown in FIG. 2, sample granulations achieved particle size distribution peaks at 80 mesh and 200 mesh. Scanning Electron Microscope (SEM) micrographs for six granulations referenced in FIGS. 1-2 are shown in FIGS. 3-8, revealing a more tightly packed particle structure, a larger surface area and an increased porosity relative to commercially available calcium carbonate granulations shown in FIGS. 9-10.

Figure 11:
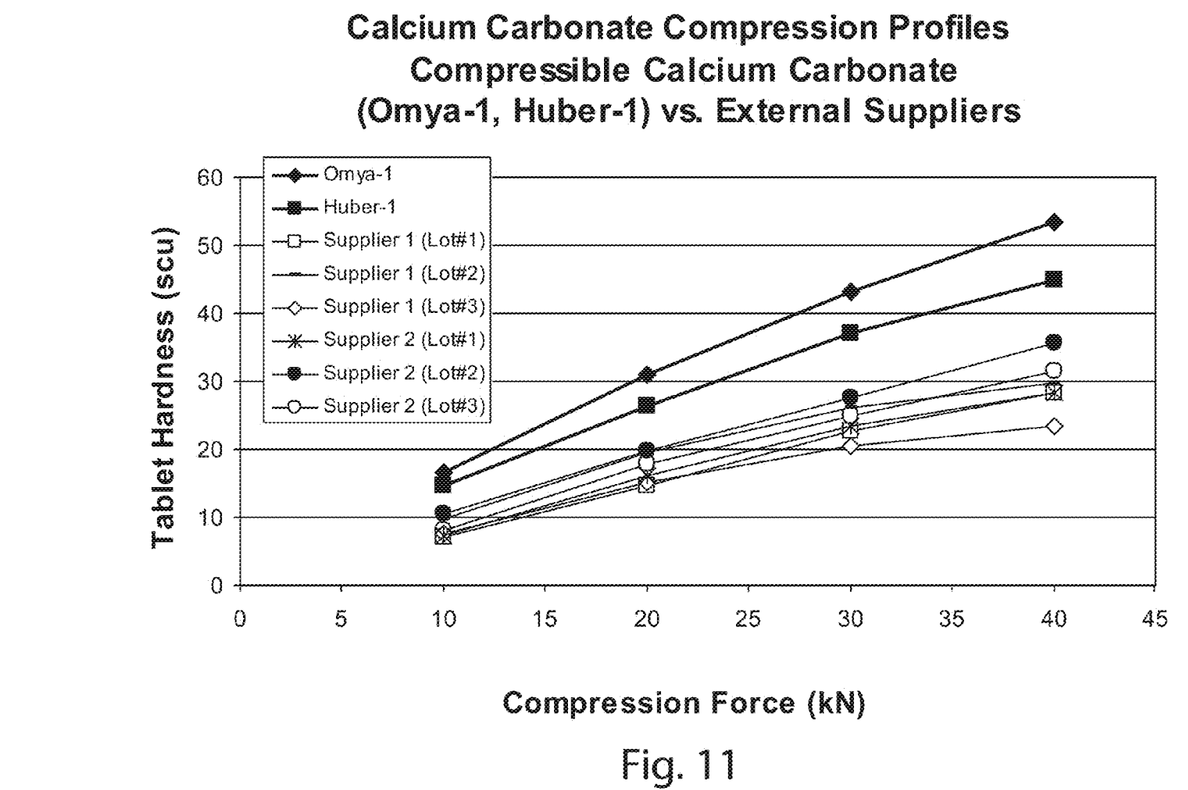
FIG. 11 is a first graph illustrating granulation compressibility.

Granulations formed in accordance with present embodiments can require lesser compaction forces to achieve a given tablet hardness. As shown in FIG. 11 for example, highly compressible, low density calcium carbonate granulations (e.g., Huber-1 and Omya-1 from FIGS. 3-4) exhibited an increase in tablet hardness of 26% to 129% at various compression forces between 10 kN and 40 kN compared to commercially available calcium carbonate granulations. The compressible calcium carbonate granulations potentially reduce product cost and tablet size by enabling the formulation of tablets with less binder excipients.

The current embodiments are further illustrated in the following examples, which are intended to be non-limiting.

Example 1

This example describes the preparation and evaluation of a calcium carbonate granulation using a Strea-1 fluid-bed granulator (GEA Process Engineering, Inc.). Powdered calcium carbonate with a mean particle size of 15 microns (OmyaCal® FG-15) was fluidized within a granulator expansion chamber and wetted with a binder solution and simultaneously dried with air heated to 180° F. The binder solution was formulated with substantially equal parts by weight of maltodextrin and acacia. The binder solution at a temperature of about 149° F. was dispersed at 16.6 g/min through single nozzle (lower position) with a 2.0 bar nozzle pressure until exhausted.

The dried granulation (0.5 kg batch) included 2.85% of maltodextrin by weight and 2.85% of acacia by weight. The dried granulation included a bulk density of 0.547 g/cm$^3$ and a tapped density of 0.67 g/cm$^3$, with a particle size distribution peak at 200 mesh as shown in Table 1 below:

TABLE 1

| Particle Size | (%) |
| --- | --- |
| 20 mesh | 0 |
| 40 mesh | 0.1 |
| 60 mesh | 2.5 |
| 80 mesh | 12.5 |
| 100 mesh | 18.7 |
| 200 mesh | 51.0 |
| Fines | 15.2 |

Sometimes in this application, density is referred to as "bulk density." To obtain this density, a 100 ml graduated cylinder is filled to a 100 ml volume with the material noted, and the weight is recorded. The density measured is referred to as the "bulk density" herein. At other times in this application, density is referred to as "tapped density." To obtain tapped density, the above process is repeated, and the graduated cylinder is then tapped 100 times in a Vanderkamp Tap Density Test, Model#10700 (Vankel Industries, Inc., Edison, N.J.). The density measured after such tapping is referred to as the "tapped density" herein.

The dried granulation was compacted into tablets using a Kikusui Vela G Tablet Press, available from Kikusui Seisakusho Ltd of Kyoto, Japan with a 0.62% magnesium substrate at 10, 20, 30 and 40 kN and at 40 rpm. As shown in FIG. 11, the dried granulation exhibited a 50% to 129% improvement in tablet hardness over commercially available granulations at various compaction forces between about 10 kN and 40 kN. The hardness for 500 mg tablets with ⅜" round tooling is shown in Table 2 below:

TABLE 2

| Granulation Compressibility | |
| --- | --- |
| Compression Force (kN) | Tablet Hardness (scu) |
| 10 | 17 |
| 20 | 31 |
| 30 | 43 |
| 40 | 53 |

Figure 12:
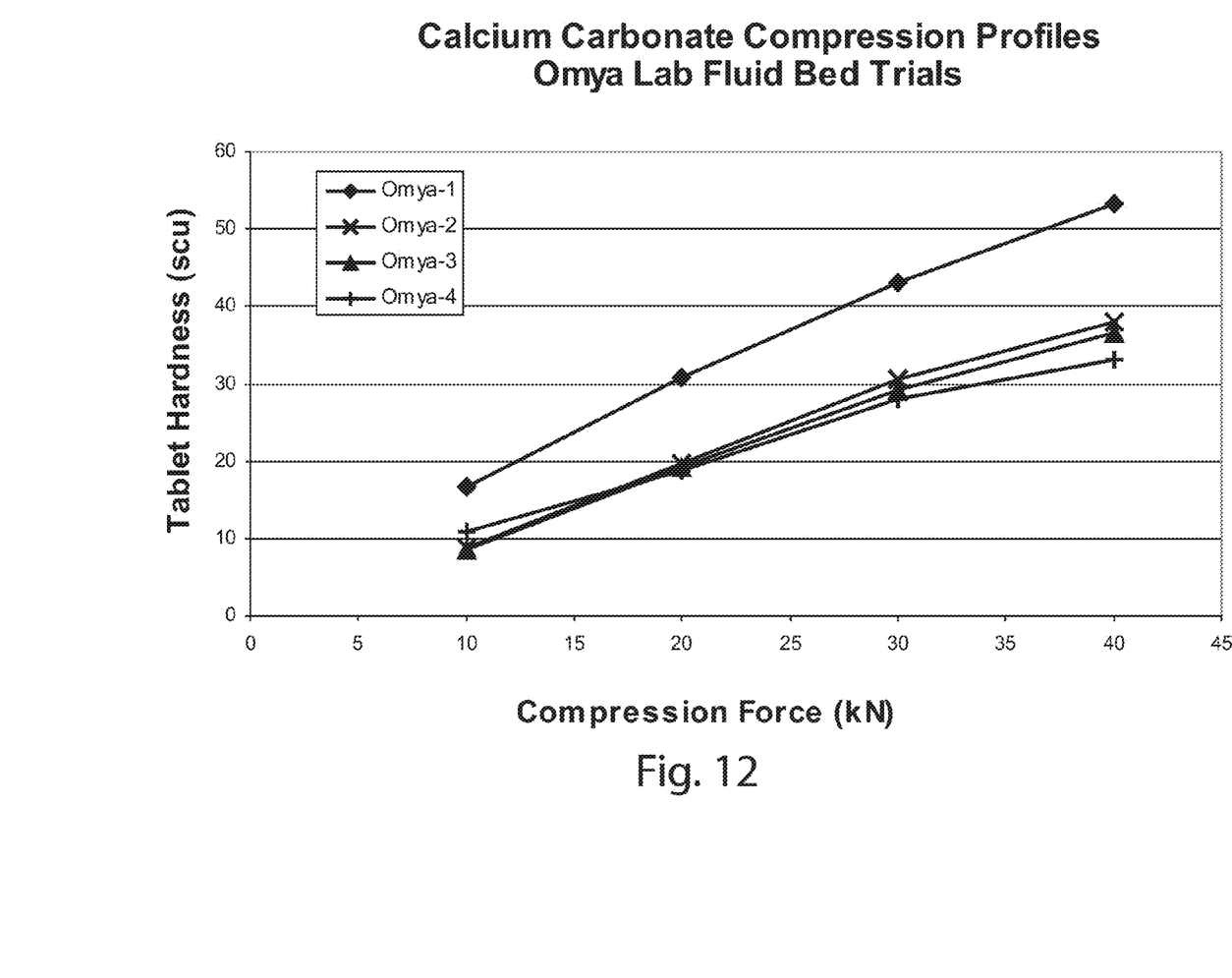
FIG. 12 is a second graph illustrating granulation compressibility.

Other trials were run at higher spray rates and/or lower atomization pressures and produced granulation with larger particle sizes and higher densities and lower compressibility as shown in FIG. 12.

Example 2

This example describes the preparation and evaluation of a calcium carbonate granulation according to the fluidized bed process of Example 1. Powdered calcium carbonate having a median particle size of 15 μm (HuberCal® 250 Calcium Carbonate) was fluidized within an expansion chamber and wetted with the binder solution and simultaneously dried with air heated to 180° F. The binder solution was formulated with substantially equal parts by weight of maltodextrin and acacia. The binder solution was dispersed at 16.6 g/min through single nozzle (lower position) with a 2.0 bar nozzle pressure until exhausted.

The dried granulation (0.5 kg batch) included 2.85% of maltodextrin by weight and 2.85% of acacia by weight. The dried granulation included a bulk density of 0.69 g/cm$^3$, a tapped density of 0.86 g/cm$^3$, with particle size distribution peaks at 80 and 200 mesh as shown in Table 3 below:

TABLE 3

| Particle Size | (%) |
|---|---|
| 20 mesh | 0 |
| 40 mesh | 0 |
| 60 mesh | 11.3 |
| 80 mesh | 22.8 |
| 100 mesh | 19.1 |
| 200 mesh | 37.1 |
| Fines | 9.7 |

The dried granulation was compacted into tablets using a Kikusui Vela G Tablet Press, available from Kikusui Seisakusho Ltd of Kyoto, Japan with a 0.62% magnesium substrate at 10, 20, 30, and 40 kN and at 40 rpm. As shown in FIG. 11, the dried granulation exhibited a 26% to 94% improvement in tablet hardness over commercially available granulations at various compaction forces between about 10 kN and 40 kN. The hardness for 500 mg tablets with ⅜" round tooling is shown in Table 4 below:

TABLE 4

| Granulation Compressibility | |
|---|---|
| Compression Force (kN) | Tablet Hardness (scu) |
| 10 | 15 |
| 20 | 27 |
| 30 | 37 |
| 40 | 45 |

Figure 13:
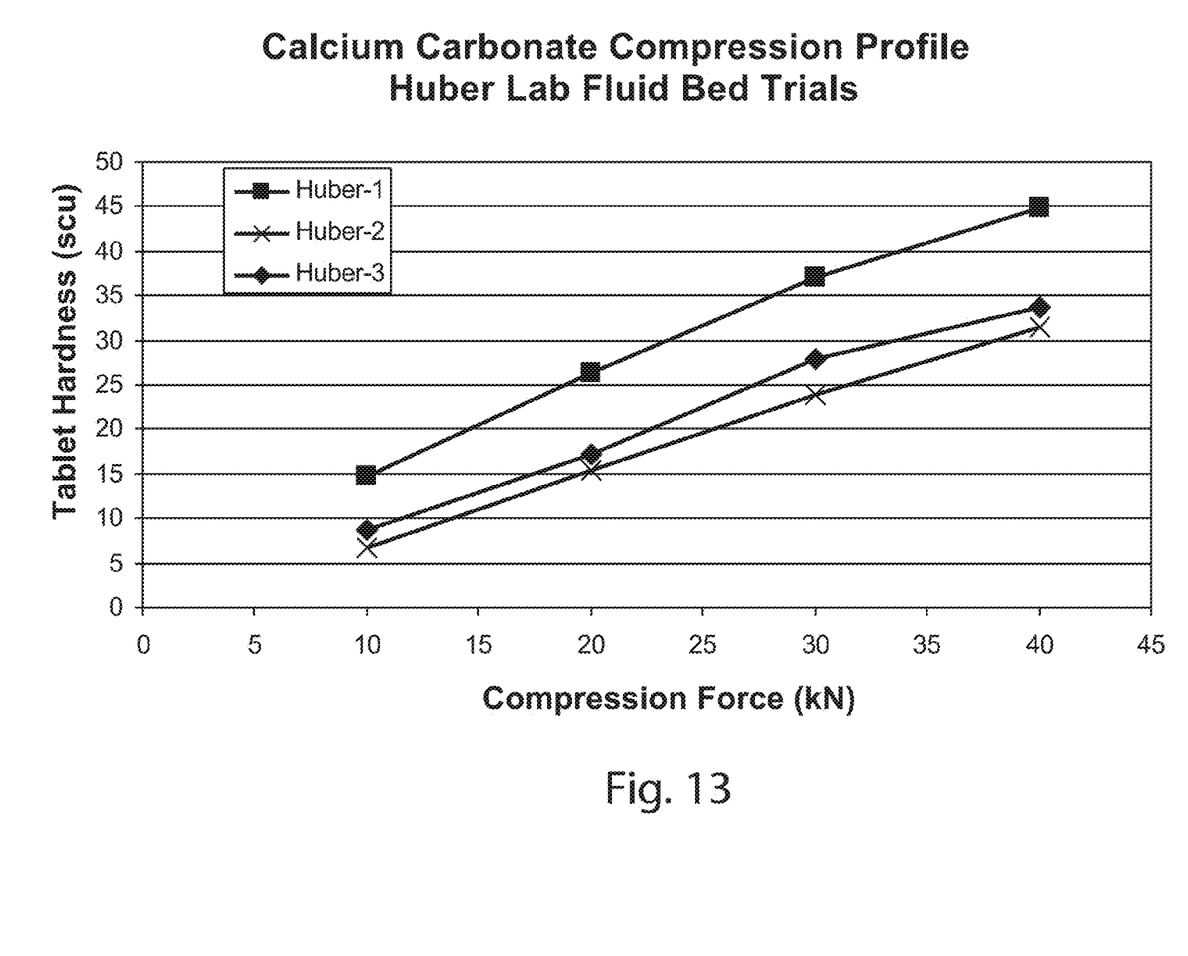
FIG. 13 is a third graph illustrating granulation compressibility.

Other trials were run at higher spray rates and/or lower atomization pressures produced granulation with larger particle sizes and higher densities and lower compressibility as shown in FIG. 13.

Example 3

This example describes the preparation and evaluation of a calcium carbonate granulation using a FL-M-15 fluid-bed granulator (Freund-Vector Corporation). Powdered calcium carbonate with a median particle size of 15 microns (Omya-Cal® FG-15) was fluidized within a granulator expansion chamber and wetted with a binder solution. The binder solution was formulated with substantially equal parts by weight of maltodextrin and acacia. The binder solution was dispersed at 125 g/min through a single nozzle (middle position) with a 39 psi nozzle pressure. The granulation was dried with inlet air heated to about 65° C. to 80° C. and the product temperature maintained at about 35° C. to 55° C.

The dried granulation (31 kg batch) included 2.85% of maltodextrin by weight and 2.85% of acacia by weight. The dried granulation included a bulk density of 0.591 g/cm$^3$ and a tapped density of 0.73 g/cm$^3$, with particle size distribution peaks at 80 mesh and 200 mesh as shown in Table 5 below:

TABLE 5

| Particle Size | (%) |
|---|---|
| 20 mesh | 0 |
| 40 mesh | 3.0 |
| 60 mesh | 18.0 |
| 80 mesh | 35.0 |
| 100 mesh | 15.0 |
| 200 mesh | 26.0 |
| Fines | 3.0 |

Figure 14:
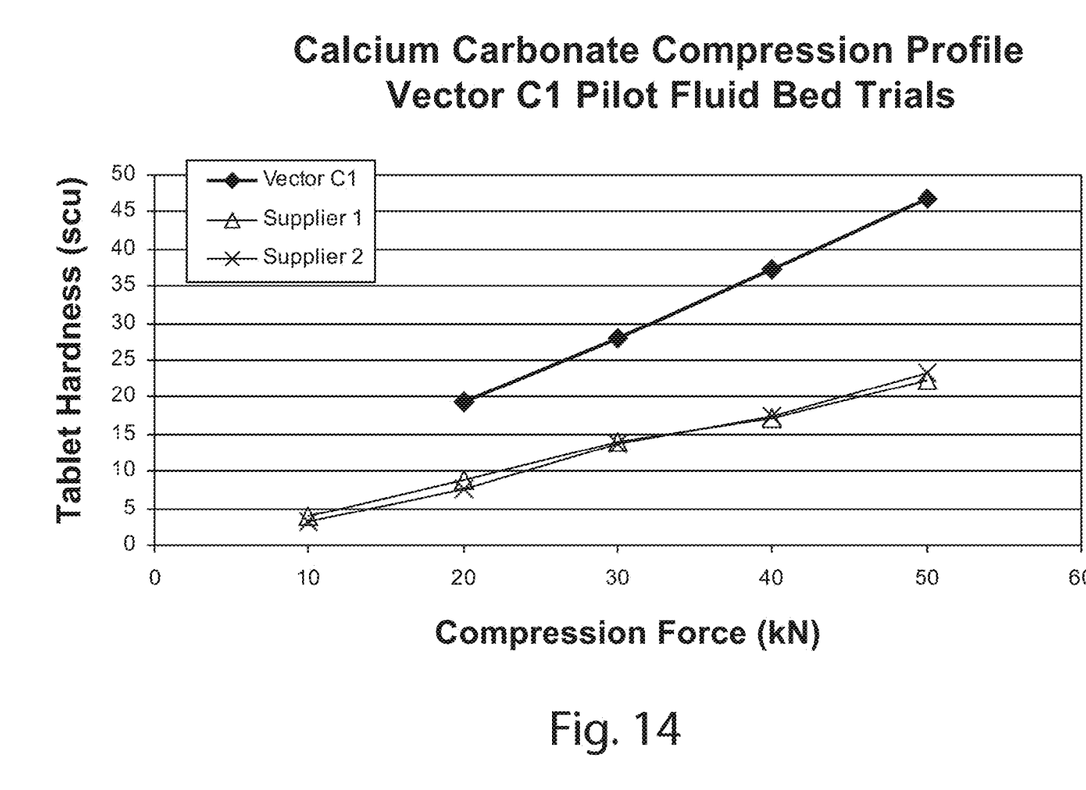
FIG. 14 is a fourth graph illustrating granulation compressibility.

The dried granulation was compacted into tablets using a Kikusui Libra Tablet Press, available from Kikusui Seisakusho Ltd of Kyoto, Japan with a 0.62% magnesium substrate at 20, 30, 40 and 50 kN and at 40 rpm. As shown in FIG. 14, the dried granulation exhibited a 50% to 151% improvement in tablet hardness over commercially available granulations at various compaction forces between about 20 kN and 50 kN. The hardness for 1000 mg tablets with ½" round tooling is shown in Table 6 below:

TABLE 6

| Granulation Compressibility | |
|---|---|
| Compression Force (kN) | Tablet Hardness (scu) |
| 20 | 19 |
| 30 | 28 |
| 40 | 37 |
| 50 | 47 |

Figure 15:
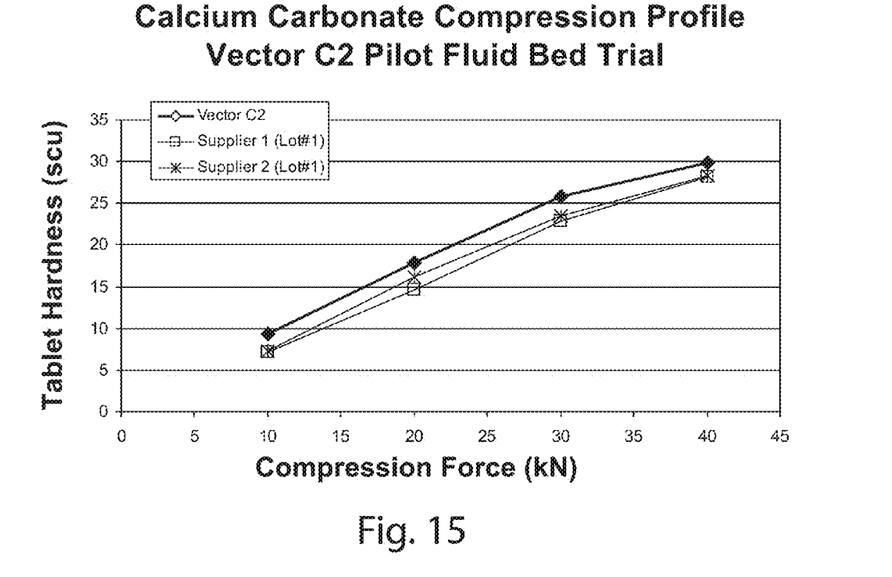
FIG. 15 is a fifth graph illustrating granulation compressibility.
Figure 16:
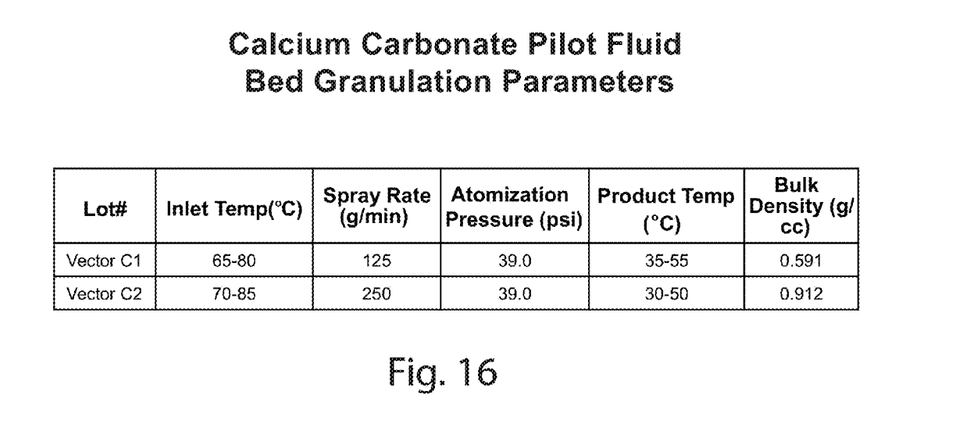
FIG. 16 is a table illustrating pilot fluid bed granulation parameters in accordance with current embodiments.
Figure 17:
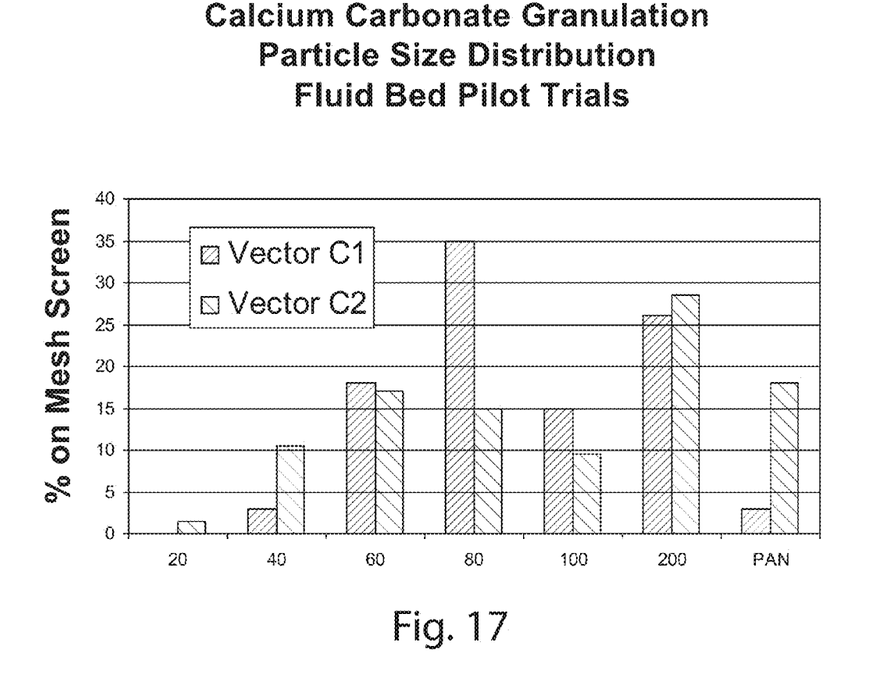
FIG. 17 is a bar graph illustrating particle size distributions for the granulations of FIG. 16.

A second trial (Vector C2) was run at a higher spray rate of 250 g/min through a single nozzle (middle position) with a 39 psi nozzle pressure. The granulation was dried with inlet air heated to about 70 to 85° C. and the product temperature maintained at about 30 to 50° C. These conditions produced a granulation with larger particle sizes, higher densities and lower compressibility as shown in FIGS. 15, 16, and 17.

The above description is that of current embodiments. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The invention claimed is:

1. A method comprising:
applying an atomized binder solution in a fluid bed granulator to a fluidized powdered calcium carbonate, the atomized binder being discharged from an outlet with an atomization pressure of at least 1.5 bar;
drying the resulting composition with a fluid heated to between about 130° F. and about 200° F. to produce a compressible calcium carbonate granulation having a bulk density of less than 0.8 g/cm3; and
compacting the granulation with a force of not more than 30 kN to achieve a tablet having a hardness of at least 28 Strong-Cobb units (scu).

2. The method of claim 1 wherein the atomized binder is applied with a spray rate of between 125 g/min and 200 g/min.

3. The method of claim 1 wherein the compressible granulation includes binder present in an amount of about 1.0% to about 25.0% by weight of the compressible granulation.

4. The method of claim 1 wherein the binder solution includes maltodextrin and a hydrocolloid binder.

5. The method of claim 1 wherein the compressible granulation includes a mean particle size of between about 50 microns and about 175 microns.

6. The method of claim 1 wherein the binder solution is heated to at least 110° F.

7. The method of claim 1 wherein compacting the granulation with a force of not more than 30 kN to achieve a tablet having a hardness of at least 28 scu includes achieving a hardness of at least 40 scu.

8. A method for preparing a calcium carbonate granulation, comprising:
providing a particulate composition comprising powdered calcium carbonate and an atomized binder;
drying the particulate composition in a fluidized bed dryer with inlet air being between about 130° F. and about 200° F. to provide a granulation having a bulk density of less than 0.8 g/cm$^3$; and
compacting the granulation with a force of not more than 30 kN to achieve a tablet having a hardness of at least 28 Strong-Cobb units (scu).

9. The method of claim 8 wherein the atomized binder is applied through a pressure nozzle at a pressure between about 1.5 bar and about 4.4 bar.

10. The method of claim 8 wherein the atomized binder is applied at a spray rate of between 125 g/min and 200 g/min.

11. The method of claim 8 wherein the composition comprising the powdered calcium carbonate and the atomized binder includes about 1.0% to about 25.0% atomized binder by weight of the composition.

12. The method of claim 8 wherein the composition comprising the powdered calcium carbonated and the atomized binder includes maltodextrin present in an amount between about 2% and about 8% by weight of the composition and a hydrocolloid present in an amount between about 2% and about 8% by weight of the composition.

13. The method of claim 8 wherein composition comprising the powdered calcium carbonated and the atomized binder includes equal parts by weight of maltodextrin and acacia.

14. The method of claim 8 wherein the granulation includes a mean particle size of between about 80 mesh and about 200 mesh.

15. The method of claim 8 wherein compacting the granulation into a tablet having a hardness of greater than 28 scu for a compression force of 30 kN includes achieving a hardness of greater than 40 scu.

16. The method of claim 1 wherein the atomized binder solution includes maltodextrin and acacia.

17. The method of claim 16 wherein the compressible granulation includes equal parts by weight maltodextrin and acacia.

18. The method of claim 16 wherein the compressible granulation includes between about 2% and about 4% by weight maltodextrin and between about 2% and about 4% by weight acacia.

19. The method of claim 1 wherein the atomized binder solution includes a binder selected from the group consisting of maltodextrin, dextrin, ethylcellulose, methylcellulose, hypromellose, hydroxylpropyl cellulose, sodium carboxymethyl cellulose, polyvinylpyrrolidone, acacia, alginates, carrageenan, dextran, furcellaran, pectin, gelatin, gum agar, locust bean gum, gum ghatti, guar gum, tragacanth, gum Arabic, xanthan gum, karaya gum, tara gum, cellulose derivatives, starch derivatives and combinations thereof.

20. The method of claim 8 wherein the atomized binder includes a binder selected from the group consisting of maltodextrin, dextrin, ethylcellulose, methylcellulose, hypromellose, hydroxylpropyl cellulose, sodium carboxymethyl cellulose, polyvinylpyrrolidone, acacia, alginates, carrageenan, dextran, furcellaran, pectin, gelatin, gum agar, locust bean gum, gum ghatti, guar gum, tragacanth, gum Arabic, xanthan gum, karaya gum, tara gum, cellulose derivatives, starch derivatives and combinations thereof.

* * * * *

UNITED STATES PATENT AND TRADEMARK OFFICE
CERTIFICATE OF CORRECTION

PATENT NO.        : 8,821,942 B1
APPLICATION NO.   : 13/440309
DATED             : September 2, 2014
INVENTOR(S)       : Chang et al.

Page 1 of 1

It is certified that error appears in the above-identified patent and that said Letters Patent is hereby corrected as shown below:

In the Claims,

Column 9, Claim 8, Line 34
"granulation" should be --tablet--

Signed and Sealed this
Seventeenth Day of February, 2015

Michelle K. Lee
*Deputy Director of the United States Patent and Trademark Office*